(12) United States Patent
Allen et al.

(10) Patent No.: US 7,303,764 B2
(45) Date of Patent: *Dec. 4, 2007

(54) 2-METHYL-THIENO-BENZODIAZEPINE FORMULATION

(75) Inventors: Douglas J. Allen, Indianapolis, IN (US); Kurt D. Dekemper, Franklin, IN (US); Thomas H. Ferguson, Greenfield, IN (US); Stuart J. Garvin, Plainfield, IN (US); Linda C. Murray, Noblesville, IN (US); Norman D. Brooks, Greenfield, IN (US); Charles A. Bunnell, Lafayette, IN (US); Snehlata S. Mascarenhas, Indianapolis, IN (US); Sharon L. Shinkle, Indianapolis, IN (US); Barry A. Hendriksen, Guildford (GB); David E. Tupper, Reading (GB); Manuel V. Sanchez-Felix, Grayshott (GB)

(73) Assignee: Eli Lilly and Company, Indianapolis, IN (US)

( * ) Notice: Subject to any disclaimer, the term of this patent is extended or adjusted under 35 U.S.C. 154(b) by 177 days.

This patent is subject to a terminal disclaimer.

(21) Appl. No.: 10/613,619

(22) Filed: Jul. 3, 2003

(65) Prior Publication Data

US 2004/0097489 A1 May 20, 2004

Related U.S. Application Data

(63) Continuation of application No. 10/136,887, filed on May 1, 2002, now Pat. No. 6,617,321, which is a continuation of application No. 09/509,757, filed as application No. PCT/US98/20426 on Sep. 30, 1998, now abandoned.

(60) Provisional application No. 60/060,493, filed on Sep. 30, 1997.

(51) Int. Cl.
*A61K 9/14* (2006.01)
*A61K 31/55* (2006.01)
(52) U.S. Cl. .................. 424/489; 514/220
(58) Field of Classification Search .............. 424/489, 424/465, 468, 423; 514/220
See application file for complete search history.

(56) References Cited

U.S. PATENT DOCUMENTS

| | | | |
|---|---|---|---|
| 3,354,036 A | 11/1967 | Jelinek | |
| 3,676,557 A | 7/1972 | Lachman et al. | |
| 3,904,670 A | 9/1975 | Ricard et al. | |
| 3,956,330 A | 5/1976 | Corey, Jr. et al. | |
| 4,016,273 A | 4/1977 | Sieger et al. | |
| 4,076,942 A | 2/1978 | Smith et al. | |
| 4,320,124 A | 3/1982 | Koe | |
| H672 H * | 9/1989 | Baxter et al. | 424/433 |
| 4,977,150 A | 12/1990 | Chakrabarti et al. | |
| 5,229,382 A | 7/1993 | Chakrabarti et al. | |
| 5,292,760 A * | 3/1994 | Martin et al. | 514/357 |
| 5,439,688 A | 8/1995 | Orsolini et al. | |
| 5,605,897 A | 2/1997 | Beasley, Jr. et al. | |
| 5,612,346 A | 3/1997 | Mesens et al. | |
| 5,639,480 A | 6/1997 | Bodmer et al. | |
| 5,723,467 A | 3/1998 | Mesens et al. | |
| 5,736,152 A | 4/1998 | Dunn | |
| 5,736,541 A | 4/1998 | Bunnett et al. | |
| 5,773,032 A | 6/1998 | Engel et al. | |
| 5,776,885 A | 7/1998 | Orsolini et al. | |
| 5,776,928 A | 7/1998 | Beasley, Jr. | |
| 6,169,084 B1 | 1/2001 | Bunnett et al. | |
| 6,617,321 B2 * | 9/2003 | Allen et al. | 514/220 |

FOREIGN PATENT DOCUMENTS

| | | |
|---|---|---|
| EP | 0568096 A1 | 11/1993 |
| GB | 1 539 277 | 1/1979 |
| WO | WO 96/29995 | 10/1996 |
| WO | WO 96/30375 | 10/1996 |
| WO | WO 98/11893 | 3/1998 |
| WO | WO 2006/073886 A1 | 7/2006 |

OTHER PUBLICATIONS

Second College Edition, The American Heritage Dictionary, 1976, p. 866.*
Hugarian Search Report, App. No. P 00 04534, X-11666.
E. Saias et al. A class of oral retard and sustained effect drugs: the pamoates, *Annales Pharmaceutiques Francaises*, 1969, pp. 557-570, 27(9-10).
Harold L. Goldberg., M.D. et al, A Double-Blind Study of Tofranil Pamoate vs. Tofranil Hydrochloride, *Psychosomatics*, Mar.-Apr. 1972, pp. 131-134, vol. XIII.
William C. Miller, Jr. et al., A Controlled Study of Single-Dose Administration of Imipramine Pamoate in Endogenous Depression, *Current Therapeutic Research*, Oct. 1973, pp. 700-706, 15(10).
A. T. Florence et al., Effect of Formulation of Intramuscular Injections of Phenothiazines on Duration of Activity, *Journal of Pharmaceutical Sciences*, Nov. 1976, pp. 1665-1668, 65(11).
Stephen M. Berge et al., Pharmaceutical Salts, *Journal of Pharmaceutical Science*, Jan. 1977, pp. 1-19, 66(1).
Philip L. Gould, Salt selection for basic drugs, *International Journal of Pharmaceutics*, 1986, pp. 201-217, 33.
H. C. Caldwell et al., Latentiation of Dihydrostreptomycin by Pamoate Formation, *Journal of Pharmaceutical Sciences*, 1970, pp. 1689-1690, 59.

* cited by examiner

*Primary Examiner*—Michael G. Hartley
*Assistant Examiner*—Blessing Fubara
(74) *Attorney, Agent, or Firm*—Nelson L. Lentz

(57) ABSTRACT

The invention provides a pharmaceutically acceptable oleaginous or cholesterol microsphere formulation of olanzapine or olanzapine pamoate or solvates thereof. The invention further provides novel olanzapine pamoate salts or solvates thereof.

16 Claims, No Drawings

2-METHYL-THIENO-BENZODIAZEPINE FORMULATION

This is a continuation application of U.S. application Ser. No. 10/136,887, filed May 1, 2002 now U.S. Pat. No. 6,617,321, which is a continuation application of U.S. application Ser. No. 09/509,757, filed Mar. 29, 2000, now abandoned which is a 371 of PCT/US98/20426 filed Sep. 30, 1998 which claims priority to U.S. Provisional Application No. 60/060,493 filed Sep. 30, 1997.

This invention provides a pharmaceutically elegant formulation of 2-methyl-4-(4-methyl-1-piperazinyl)-10H-thieno[2,3-b][1,5]benzodiazepine, (hereinafter referred to as "olanzapine") or a pamoate salt or solvate thereof.

Olanzapine has shown great promise in the treatment of psychotic patients and is currently being marketed for that purpose. Such psychotic patients are often non-compliant, making it difficult to assess whether or not a patient has received the proper dosage of medication. Applicants have discovered that it can be especially desired to Formulate olanzapine in a depot formulation or as a quick intramuscular formulation to assure consistent and proper dosage of the drug substance and to assume compliance.

Such formulation must be carefully designed and selected due to olanzapine's tendency to be metastable, to undergo pharmaceutically undesired discoloration, and olanzapine's surprising potency which requires care to assure homogeniety and stability of the finished formulation.

Typically, the artisan would prepare an ester form of the active drug substance to provide sustained release. Unfortunately, the olanzapine molecule is not amenable to formation of the ester product.

In addition, Applicants have discovered that olanzapine undergoes undesirable discoloration when contacted with certain excipients including powder blends. The discoloration is exacerbated by ambient air conditions, at elevated temperatures, and by moist environments. Although the discoloration phenomenon may not produce an increase in the number of total related substances, the color change is not generally considered pharmaceutically acceptable for commercial purposes.

In addition, it is known that the pH of muscle tissue can vary with exercise, stress, and injury which can affect drug solubility, and thus the rate of absorption of injectable drugs. Therefore, it is desirable to find an injectable sustained release formulation in which the release rate of the active ingredient is minimally dependent on pH.

Applicants have discovered that a formulation comprising olanzapine or a pamoate salt or solvate thereof as an active ingredient, and one or more carriers, can address the long felt need for such stable, pharmaceutically elegant formulation with a controllable release rate which may be useful as a depot formulation or for fast acting intramuscular or subcutaneous use.

The present invention provides a formulation comprising olanzapine or a pamoate salt or solvate thereof, and an oleaginous or cholesterol microsphere carrier.

The present invention provides, in addition, novel pamoate salts of olanzapine. Such salts are especially useful in preparing a sustained release formulation in which the release rate is minimally dependent on the pH of the environment.

Olanzapine may be used. However, Applicants have discovered that pamoate salts of olanzapine may be preferred in effecting duration of release from the above compositions. Different solvate forms of olanzapine or its pamoate salts may also be useful, including, for example, olanzapine dihydrates D, E and F, olanzapine pamoate, and the monohydrate, dimethanolate, THF (tetrahydrofuran) and acetone solvates of olanzapine pamoate. Bis(olanzapine) pamoate and its solvates may also be useful in the current invention. A preferred salt is olanzapine pamoate monohydrate. Bis(olanzapine) pamoate monohydrate is also a preferred salt.

The formulation may contain the most stable anhydrous form of olanzapine, referred to herein as Form II; however, other forms of olanzapine are contemplated.

A typical example of an x-ray diffraction pattern for Form II is as follows wherein d represents the interplanar spacing and intensity represents the typical relative intensities as set forth in Table 1:

TABLE 1

| d-spacings | Intensity |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out above were obtained using a Siemens D5000 x-ray powder diffractometer having a copper $K_a$ radiation source of wavelength, $1=1\cdot541$ Å.

An especially preferred olanzapine pamoate solvate is the pamoate monohydrate having a typical x-ray powder diffraction pattern as represented by the following interplanar d-spacings and relative intensities as set forth in Table 2

TABLE 2

| Olanzapine Pamoate Monohydrate | |
|---|---|
| d-spacing | Intensity |
| 10.76 | 98 |
| 9.20 | 62 |
| 8.38 | 85 |
| 8.18 | 24 |
| 7.62 | 20 |
| 6.67 | 18 |
| 6.56 | 18 |
| 6.51 | 20 |
| 6.44 | 20 |
| 6.11 | 26 |
| 5.88 | 22 |

TABLE 2-continued

Olanzapine Pamoate Monohydrate

| d-spacing | Intensity |
|---|---|
| 5.64 | 15 |
| 5.38 | 100 |
| 4.90 | 11 |
| 4.72 | 12 |
| 4.64 | 17 |
| 4.48 | 18 |
| 4.35 | 23 |
| 4.29 | 31 |
| 4.24 | 32 |
| 4.09 | 71 |
| 4.02 | 84 |
| 3.98 | 73 |
| 3.81 | 23 |
| 3.62 | 14 |
| 3.52 | 30 |
| 3.39 | 11 |
| 3.25 | 12 |
| 2.90 | 15 |
| 2.85 | 13 |

Another especially preferred olanzapine pamoate solvate is pamoate dimethanolate having a typical x-ray powder diffraction pattern as represented by the following interplanar d-spacings and relative intensities as set forth in Table 3.

TABLE 3

Olanzapine Pamoate Dimethanolate

| d-spacing | Intensity |
|---|---|
| 11.17 | 73 |
| 9.37 | 17 |
| 8.73 | 40 |
| 8.29 | 23 |
| 7.77 | 14 |
| 7.22 | 24 |
| 6.84 | 31 |
| 6.66 | 54 |
| 6.42 | 11 |
| 6.40 | 11 |
| 6.17 | 26 |
| 5.87 | 12 |
| 5.56 | 100 |
| 4.84 | 11 |
| 4.66 | 17 |
| 4.57 | 26 |
| 4.48 | 22 |
| 4.35 | 19 |
| 4.28 | 19 |
| 4.12 | 94 |
| 4.03 | 91 |
| 3.89 | 52 |
| 3.62 | 44 |
| 3.54 | 11 |
| 3.29 | 16 |
| 3.13 | 16 |

Yet another preferred olanzapine pamoate solvate is the pamoate THF solvate having a typical x-ray powder diffraction pattern as represented by the following interplanar d-spacings and relative intensities as set forth in Table 4.

TABLE 4

Olanzapine THF Solvate

| d-spacing | Intensity |
|---|---|
| 14.59 | 100 |
| 7.78 | 16 |

TABLE 4-continued

Olanzapine THF Solvate

| d-spacing | Intensity |
|---|---|
| 7.24 | 56 |
| 7.00 | 19 |
| 6.37 | 12 |
| 6.04 | 11 |
| 6.01 | 11 |
| 4.85 | 19 |
| 4.69 | 42 |
| 4.39 | 25 |
| 4.28 | 19 |
| 3.95 | 13 |
| 3.84 | 20 |

Still another especially preferred olanzapine pamoate solvate is the bis(olanzapine) pamoate acetone solvate having a typical x-ray powder diffraction pattern as represented by the following interplanar d-spacings and relative intensities as set forth in Table 5.

TABLE 5

Olanzapine Pamoate Acetone Solvate

| d-spacing | Intensity |
|---|---|
| 16.87 | 32 |
| 9.58 | 35 |
| 8.88 | 80 |
| 8.40 | 16 |
| 8.19 | 35 |
| 7.85 | 16 |
| 7.34 | 29 |
| 7.22 | 25 |
| 7.04 | 30 |
| 6.87 | 18 |
| 6.77 | 11 |
| 6.73 | 11 |
| 6.65 | 21 |
| 6.36 | 12 |
| 6.26 | 26 |
| 5.76 | 31 |
| 5.58 | 79 |
| 5.53 | 100 |
| 5.45 | 61 |
| 5.32 | 42 |
| 5.19 | 39 |
| 5.02 | 55 |
| 4.91 | 69 |
| 4.87 | 51 |
| 4.85 | 57 |
| 4.69 | 44 |
| 4.61 | 68 |
| 4.44 | 23 |
| 4.34 | 14 |
| 4.18 | 17 |
| 4.07 | 36 |
| 3.99 | 28 |
| 3.93 | 65 |
| 3.81 | 23 |
| 3.78 | 24 |
| 3.77 | 20 |
| 3.65 | 23 |
| 3.59 | 28 |
| 3.45 | 13 |
| 3.32 | 19 |
| 3.25 | 26 |

An additional especially preferred olanzapine pamoate solvate is bis(olanzapine) pamoate monohydrate having a typical x-ray powder diffraction pattern as represented by the following interplanar d-spacings and relative intensities as set forth in Table 6.

TABLE 6

Bis(Olanzapine) Monohydrate

| d-spacing | Intensity |
|---|---|
| 15.77 | 26 |
| 10.44 | 23 |
| 9.64 | 24 |
| 9.31 | 13 |
| 8.27 | 23 |
| 8.17 | 14 |
| 8.13 | 14 |
| 7.84 | 27 |
| 7.81 | 30 |
| 7.41 | 60 |
| 7.12 | 40 |
| 7.00 | 13 |
| 6.96 | 13 |
| 6.55 | 45 |
| 6.18 | 53 |
| 5.87 | 38 |
| 5.80 | 19 |
| 5.59 | 89 |
| 5.25 | 26 |
| 5.00 | 34 |
| 4.96 | 31 |
| 4.88 | 61 |
| 4.85 | 73 |
| 4.71 | 34 |
| 4.52 | 19 |
| 4.33 | 11 |
| 4.19 | 100 |
| 4.12 | 48 |
| 4.05 | 39 |
| 3.97 | 30 |
| 3.89 | 31 |
| 3.80 | 29 |
| 3.72 | 20 |
| 3.70 | 21 |
| 3.58 | 33 |
| 3.45 | 27 |
| 3.04 | 13 |
| 2.84 | 16 |

The X-Ray powder diffraction patterns for the pamoate salts and solvates were collected on a Siemens D5000 Diffractometer, using Cu Kα radiation at a wavelength of 1.5406 Å. Instrumental conditions: stepsize 0.01°; scan rate 1.0 seconds/step; range 4°–35° 2θ; 0.6 mm divergence slit; 1.0 mm scattered radiation slit; 0.2 mm receiving slit; 50 kV; 40 mA; Kevex solid state detector. Samples were packed into recessed sample holders for analysis.

The formulation of the invention may contain substantially pure Form II as the active ingredient. As used herein "substantially pure" refers to Form II associated with less than about 15% undesired polymorphic form of olanzapine (herein referred to as "Undesired Form"), preferably less than about 5% Undesired Form, and more preferably less than about 2% Undesired Form. Further, "substantially pure" Form II will contain less than about 5% undesired chemical impurities or residual solvent or water. In particular, "substantially pure" Form II preferably contain less than about 0.05% content of acetonitrile, more preferably, less than about 0.005% content of acetonitrile.

Form II is the most stable anhydrous form of olanzapine known and is therefore important for the commercial development of pharmaceutically elegant formulations.

O-dihydrate refers to crystalline Dihydrate D olanzapine polymorph (herein referred to as "Dihydrate D") having a typical x-ray powder diffraction pattern as represented by the following interplanar d-spacings and relative intensities as set forth in Table 7:

TABLE 7

Olanzapine Dihydrate D

| d-spacings | Intensity |
|---|---|
| 9.4511 | 100.00 |
| 7.7098 | 14.23 |
| 7.4482 | 22.43 |
| 6.9807 | 5.73 |
| 6.5252 | 5.45 |
| 5.7076 | 4.24 |
| 5.5539 | 1.60 |
| 5.223 | 62.98 |
| 4.9803 | 22.21 |
| 4.8908 | 15.03 |
| 4.784 | 27.81 |
| 4.6947 | 5.15 |
| 4.4271 | 13.00 |
| 4.3956 | 16.63 |
| 4.3492 | 34.43 |
| 4.2834 | 51.38 |
| 4.1156 | 18.32 |
| 3.7837 | 5.30 |
| 3.7118 | 1.56 |
| 3.5757 | 0.71 |
| 3.482 | 9.39 |
| 3.3758 | 24.87 |
| 3.3274 | 13.49 |
| 3.2413 | 5.97 |
| 3.1879 | 1.04 |
| 3.135 | 3.18 |
| 3.0979 | 1.43 |
| 3.016 | 1.95 |
| 2.9637 | 0.48 |
| 2.907 | 2.42 |
| 2.8256 | 7.46 |
| 2.7914 | 3.61 |
| 2.7317 | 1.47 |
| 2.6732 | 5.19 |
| 2.5863 | 10.62 |

Another especially preferred dihydrate is the crystalline Dihydrate B olanzapine polymorph (herein referred to as "Dihydrate B") having a typical x-ray powder diffraction pattern as represented by the following interplanar d-spacings and relative Intensities as set forth in Table 8:

TABLE 8

Olanzapine Dihydrate B

| d-spacing | Intensity |
|---|---|
| 9.9045 | 100.00 |
| 6.9985 | 0.39 |
| 6.763 | 0.17 |
| 6.4079 | 0.13 |
| 6.1548 | 0.85 |
| 6.0611 | 0.99 |
| 5.8933 | 0.35 |
| 5.6987 | 0.12 |
| 5.4395 | 1.30 |
| 5.1983 | 0.67 |
| 5.0843 | 0.24 |
| 4.9478 | 0.34 |
| 4.7941 | 6.53 |
| 4.696 | 1.26 |
| 4.5272 | 2.65 |
| 4.4351 | 2.18 |
| 4.3474 | 1.85 |
| 4.2657 | 0.49 |
| 4.1954 | 0.69 |
| 4.0555 | 0.42 |

TABLE 8-continued

Olanzapine Dihydrate B

| d-spacing | Intensity |
|---|---|
| 3.9903 | 0.89 |
| 3.9244 | 1.52 |
| 3.8561 | 0.99 |
| 3.8137 | 1.44 |
| 3.7671 | 0.92 |
| 3.6989 | 1.78 |
| 3.6527 | 0.60 |
| 3.5665 | 0.34 |
| 3.4879 | 1.41 |
| 3.3911 | 0.27 |
| 3.3289 | 0.20 |
| 3.2316 | 0.31 |
| 3.1982 | 0.19 |
| 3.1393 | 0.35 |
| 3.0824 | 0.18 |
| 2.9899 | 0.26 |
| 2.9484 | 0.38 |
| 2.9081 | 0.29 |
| 2.8551 | 0.37 |
| 2.8324 | 0.49 |
| 2.751 | 0.37 |
| 2.7323 | 0.64 |
| 2.6787 | 0.23 |
| 2.6424 | 0.38 |
| 2.5937 | 0.21 |

Another preferred olanzapine dihydrate is the crystalline Dihydrate E olanzapine polymorph (herein referred to as "Dihydrate E") having a typical x-ray powder diffraction pattern as represented by the following interplanar d-spacings and relative Intensities as set forth in Table 9:

TABLE 9

Olanzapine Dihydrate E

| d-spacing | Intensity |
|---|---|
| 9.9178 | 100.00 |
| 9.6046 | 16.75 |
| 7.0163 | 2.44 |
| 6.1987 | 8.78 |
| 6.0971 | 10.62 |
| 5.9179 | 1.73 |
| 4.8087 | 50.14 |
| 4.7140 | 10.24 |
| 4.5335 | 14.20 |
| 4.4531 | 7.80 |
| 4.3648 | 3.04 |
| 4.2760 | 4.50 |
| 4.0486 | 2.76 |
| 3.8717 | 5.09 |
| 3.8292 | 13.39 |
| 3.7053 | 17.24 |
| 3.5827 | 4.82 |
| 3.4935 | 13.22 |
| 3.3982 | 2.01 |
| 3.3294 | 1.30 |
| 3.2026 | 0.98 |
| 3.1450 | 2.66 |
| 3.1225 | 1.63 |
| 3.0880 | 2.11 |
| 2.9614 | 2.49 |
| 2.9014 | 1.03 |
| 2.8695 | 2.06 |
| 2.8359 | 1.63 |
| 2.7647 | 1.95 |
| 2.7582 | 1.68 |
| 2.7496 | 1.84 |
| 2.7421 | 1.03 |

TABLE 9-continued

Olanzapine Dihydrate E

| d-spacing | Intensity |
|---|---|
| 2.7347 | 1.36 |
| 2.6427 | 2.01 |

The x-ray powder diffraction patterns set forth herein in Tables 7, 8 and 9 were obtained with a copper k of wavelength=1.541 Å. The interplanar spacings in the column marked "d" are reported in Angstroms. The detector was a Kevex silicon lithium solid state detector.

Olanzapine Dihydrate D is prepared by extensive stirring of technical olanzapine, as described in Preparation 9, under aqueous conditions. The term "aqueous conditions" refers to an aqueous solvent which may be either water or a solvent mixture comprising water and an organic solvent which is sufficiently water miscible to allow the required stoichiometric quantity of water to be present in the solvent mixture. If a solvent mixture is utilized, then the organic solvent must be removed, leaving behind the water, and/or replaced with water. The term "extensive stirring" shall be from about four (4) hours to about six (6) days; however, the artisan will appreciate that the time will vary with the reaction conditions such as temperature, pressure, and solvent. It is preferred that the aqueous conditions include an aqueous solvent.

The completion of the reaction may be monitored using x-ray powder diffraction and other such methods familiar to the skilled artisan. Several such techniques are described below.

Compound characterization methods include, for example, x-ray powder pattern analysis, thermogravimetric analysis (TGA), wetting characteristics, spraying characteristics, differential scanning calorimetery (DSC), titrametric analysis for water, and $H^1$-NMR analysis for solvent content. SEMs, porosity, residual solvents (HPLC), syringeability, light microscope particle size, surface area, IR (for solvate/crystal form) top density, friability may also be used to characterize the compound.

The olanzapine dihydrates described herein in Preparations 9, 10 and 11 are true dihydrates having two water molecules per drug molecule, wherein the water molecules are incorporated into the crystalline lattice of the dihydrate compound.

Carriers that promote slow absorption of olanzapine include both aqueous and non-aqueous compositions.

Aqueous suspensions of olanzapine, olanzapine pamoate salts or solvates thereof include the PLURONICS, such as PLURONIC F68, which at the appropriate concentrations gels at body temperature. PLURONIC concentrations in the range of 40–45% in the presence of olanzapine gels at body temperature and would be a preferred composition for this use.

Alternatively, aqueous suspensions of cellulosic or polysaccharide gums, including sodium carboxymethyl cellulose or sodium alginate, may provide prolonged release of olanzapine, olanzapine pamoate or solvates thereof. Other natural or synthetic biopolymers may be used, such as, chitosans, gelatins, collagens, haluronic acids, and the like. In addition, up to about 30% by weight of release modifying agents may be added.

Non-aqueous compositions include but are not limited to the hydrophobic PLURONICS, propylene glycols, polyethylene glycols and oleaginous formulations. Hydrophobic PLURONICS include those with a hydrophile/lipophile balance of less than 8 and may be incorporated individually with olanzapine, olanzapine pamoate salts or solvates thereof or in conjunction with up to about 30% by weight of other release modifying agents that retard absorption in the body.

Oleaginous compositions include olanzapine, olanzapine pamoate salts or solvates thereof suspended in or solubilized in oils and oils thickened with antihydration or gelling agents. These antihydration or gelling agents give the body of oil greater viscoelasticity (and therefore greater structural stability) and thereby slow down penetration of the oil by body fluids, prolonging drug absorption.

The oil is preferably chosen from oils which are readily obtainable in reasonably pure form and which are physiologically and pharmaceutically acceptable. Of course, the oil must be sufficiently refined so that it is stable in storage, does not produce a precipitate upon standing, does not have any observable chemical reactions, and has no observable physiological reactions when administered into the body. The preferred oils are vegetable oils such as soybean oil, peanut oil, sesame oil, cottonseed oil, corn oil, olive oil, caster oil, palm oil, almond oil, refined fractionated oils, such as MIGLYOL 810, MIGLYOL 812, and the like and derivatized oils, such as, MIGLYOL 840, and the like. A most preferred oil is MIGLYOL 812, a fractionated coconut oil. Other oils may be utilized provided they meet the requirements specified above.

Exemplary antihydration or gelling agents include various salts of organic acids, for instance fatty acids having from about 8 (preferably at least 10) to about 22 (preferably up to about 20) carbon atoms, e.g., aluminum, zinc, magnesium or calcium salts of lauric acid, palmitic acid, stearic acid and the like. Such salts may be mono-, di- or trisubstituted, depending upon the valence of the metal and the degree of oxidation of the metal by the acid. Particularly useful are the aluminum salts of such fatty acids. Aluminum monostearate and distearate are preferred antihydration agents. Others that may be useful include aluminum tristearate, calcium mono- and distearate, magnesium mono- and distearate and the corresponding palmitates, laurates and the like. The concentration of the these antihydration agents is usually based upon the weight of the oil plus the drug agent, and is usually between 1% and 10%, and most typically between 2% and 5% by weight. Other concentrations may be suitable on a case-by-case basis.

Waxes, natural and synthetic, lecithins, tocopherols and their esters, such as tocopherol acetate or tocopherol succinate, polyoxyethylene derivatized castor oil (e.g., CREMOPHOR EL), polyoxyethylene derivatized hydrogenated castor oil, (CREMOPHOR RH40, CREMOPHOR RH60), fatty acid esters (e.g., ethyl- and methyl oleate), cholesterol and its derivatives may also be included in oils to impart viscoelasticity or absorption attenuating effects. Waxes are preferably chosen from vegetable, animal, or synthetic sources. Preferred sources include vegetable or synthetic sources. For example, useful waxes include Carnauba wax and beeswax. Beeswax is available in various purification grades, including white wax and yellow beeswax. Other synthetic waxes or wax derivatives may be used, such as, CRODACOL CS-50, CROTHIX, POLAWAX, SYNCROWAX, polyoxyethylene sorbital beeswax derivatives (e.g., G-1726®) and the like.

Other release modifying agents may be added into the oils to either accelerate or delay drug release. These include but are not limited to oleic acid, the oleic acid esters, such as ethyl oleate, benzyl alcohol, benzyl benzoate and the like.

Release modifying additives of lecithin based compositions include but are not limited to cholesterol, ethyl cellulose, tocopherols, polyvinyl pyrrolidone, and polyethylene glycols. These additives may be added at varying concentrations of up to about 30% by weight so as to effect drug release.

The biodegradable material, sucrose diactetate hexaisobutyrate (SDHB), in solution with a pharmaceutically acceptable solvent or solvents such as ethanol and polyethylene glycol, has been used to provide prolonged release of olanzapine. Other compositions of SDHB with release modifying agents in concentrations of up to about 20% by weight, such as propylene glycol, PLURONICS, celluloses, lecithins, oils and the like may be used to modify or prolong release of olanzapine.

A preferred oleaginous formulation comprises olanzapine, or pamoate salts or solvates thereof, an oil carrier and a gelling agent or antihydration agent. Even more preferred is an oleaginous formulation comprising olanzapine pamoate monohydrate, MIGLYOL 812 and white wax.

As used herein, the term "microparticle" shall have the common meaning known to the skilled artisan. Thus, the term includes, but is in no way limited to microspheres wherein the active ingredient may be uniformly distributed throughout the carrier, or microcapsules wherein the active ingredient is surrounded by a well-defined outer shell, and the like. The microparticles can be prepared using techniques, such as complex coacervation, polymer/polymer incompatibility, interfacial polymerization, in situ polymerization, solvent evaporation/extraction, thermal and ionic gelation, spray chilling, fluidized bed, spinning disc, rotational suspension separations, spray drying, and other methods known to the artisan.

For example, cholesterol microspheres may be formed using a solvent evaporation procedure that effectively entraps olanzapine, or an olanzapine pamoate salt or solvate thereof and provides for sustained release of olanzapine in the body. The entrapment procedure consists of emulsifying an organic solution of cholesterol, the dispersed phase, and the active of interest in the processing medium, an aqueous surfactant solution. The aqueous surfactant solution allows the formation of a stable emulsion and prevents agglomeration.

Emulsification can be accomplished by general processes known to those skilled in the art, which includes but are not limited to magnetic bar agitation, blender, overhead stirrer, in-line homogenizer, static mixer, and the like.

Examples of cationic, anionic, and nonionic compounds that may be used as surfactants include, but are not limited to, polyvinyl alcohol (PVA), carboxymethyl cellulose, gelatin, polyvinyl pyrrolidone, TWEEN 80, TWEEN 20, sodium lauryl sulfate, and the like. The concentration of the surfactant should be sufficient to stabilize the emulsion. The concentration of the surfactant will effect the final size of the cholesterol microspheres. Generally, the surfactant in the aqueous medium will be from 0.1% to about 20% by weight depending on the surfactant, the solvent used to dissolve the cholesterol, and the processing medium used.

Alternatively, the processing medium may be an oil immiscible with cholesterol. Examples of suitable oils include, but are not limited to, mineral oil and silicone oil. Suitable surfactants for the oily processing medium should be chosen to stabilize the emulsion and optimize the final size of the resultant cholesterol microspheres. In addition, surfactants may be added to the dispersed phase, or cholesterol phase, to beneficially effect the emulsion stability, microsphere size and performance.

Cholesterol derivatives used to effect duration of release, include cholesterol acetate, cholesterol hemisuccinate, cholesterol oleate, cholesterol palmitate, cholesterol stearate, and the like. Cholesterol compatible additives may be used to further effect release, such as oleic acid, ethyl oleate, methyl oleate, tristearin, and the like.

The concentration of emulsifying agent, amount of agitation, stirring rate, and temperature of the stirred emulsion will effect the rate of solvent removal, size and quality of the resultant cholesterol microspheres. In general these need to be controlled to achieve injectable microspheres. Generally accepted size range for microparticles is 1–5,000 μm. A preferred microparticle size range useful for parenteral injection is 20–500 μm. A most preferred range is 30 to 200 μm. Even more preferred is 40 to 100 μm.

Briefly, an aqueous surfactant solution of polyvinyl alcohol (PVA) is made by dissolving the PVA in deionized water. Polyvinyl alcohol concentrations up to 6% are known to be effective, but may be limited if viscosity of the processing medium is too high. For this invention, a preferred polyvinyl alcohol concentration is 1%, (5 g PVA added to 500 ml deionized water.) The surfactant solution is stirred with a magnetic stir bar and warmed at 50–60° C. for several hours until all the PVA is dissolved. The solution is allowed to cool to room temperature. The PVA surfactant solution is poured into a square plastic container and stirred with an overhead stirrer at 450 RPM. Olanzapine and cholesterol are dissolved in methylene chloride. The dispersed phase is poured directly, and immediately, into PVA solution with stirring and allowed to stir for 18 hours at room temperature, to allow the methylene chloride to evaporate and the cholesterol microspheres to form.

The cholesterol microspheres may be collected by isolating the microspheres on standard mesh sieves, washed with water or other appropriate medium, and air dried. Other collection and drying methods and pharmaceutically acceptable equipment may be used and is known to those skilled in the art.

The particle size of olanzapine, olanzapine pamoate salts or solvates thereof used in the formulations of this invention may be controlled and achieved by particle size reduction methods known to those skilled in the art, such as air-jet milling. The milled drug may vary in particle size from coarse to fine, dependent on the type of formulation used and the drug release properties desired. Coarse particles have an average particle size of from about 20 to about 60 μm; medium particles from about 5 to about 20 μm; and fine particles are less than 5 μm.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

Olanzapine is effective over a wide dosage range, the actual dose administered being dependent on the condition being treated. For example, in the treatment of adult humans, dosages of from about 0.25 to 200 mg, preferably from 1 to 30 mg; and most preferably 1 to 25 mg per day may be used. Thus, the depot formulation can be adjusted to provide the desired dosage per day over a period of from several days to up to about one month.

If a multidose formulation is contemplated, additional excipients, such as a preservative, may be required. For example, preservatives such as, but not limited to, tocopheral or propyl gallate may be employed. Other preservatives include phenol, cresol, sodium benzoate and the like.

Most preferably, the olanzapine formulation is contained in packaging materials which protect the formulation from moisture and light. For example, suitable packaging materials include amber colored high density polyethylene containers, amber colored glass bottles, polypropylene syringes, and other containers, including but not limited to a blister pack with sachet, made of a material which inhibits the passage of light. Most preferably, the packaging will include a desiccant pack. The container may be sealed with an aluminum foil blister to provide the desired protection and maintain product stability.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. Generally the olanzapine pamoate salts and solvates can be prepared by mixing olanzapine and pamoic acid in a suitable solvent followed by washing and drying the resultant product. Equimolar quantities of pamoic acid and olanzapine are required for (1:1) olanzapine pamoic salts. Bis(olanzapine) pamoate salts (2:1) require two molar equivalents of olanzapine for each mole of pamoic acid.

Applicants have discovered, surprisingly, that the solubility of olanzapine pamoate and solvates are somewhat independent of pH, particularly in the range of 4 to 8. This makes such salts especially suitable for intramuscular injections since muscle pH varies with exercise, stress, metabolic state, and wound healing, at ranges generally between 7.4 and 4. In addition, bis(olanzapine) salts have the added advantage of improving drug activity per unit mass, allowing for higher resultant microparticle loadings and reduced injection volume per unit dose.

Preferably, the formulation has a prolonged sustained release of a pharmaceutically effective amount of olanzapine, or a pamoate salt or solvate thereof for a period of greater than 7 days, more preferably at least 14 days, most preferably up to 30 days with a burst release of less than 15% active ingredient. The term "burst" is understood by those skilled in the art to mean the immediate release of active ingredient. In addition, a preferred formulation is injectable through a 21 gauge needle or smaller with an injection volume of 2 ml or less. Other desirable characteristics include the use of excipients that are toxicologically and pharmaceutically acceptable. Formulations are desirable in unit dosage form suitable, preferably, for subcutaneous or intramuscular administration.

The formulations claimed herein may be used alone or in combination with one another. Depending on the carrier selected, the formulations claimed herein can be especially useful for short acting intramuscular administration or as a depot formulation. The olanzapine oleaginous carrier formulation is useful either in combination with cholesterol (up to 50% mass per unit volume) microspheres or by itself without the use of microspheres. The cholesterol microspheres may also be mixed with an oleagenous carrier and water in an amount up to and including 50% mass per unit injection volume, depending on the type of excipients used.

The following examples are provided for purposes of illustration and are not to be construed as limiting the scope of the claimed invention.

Preparation 1

Technical Grade Olanzapine

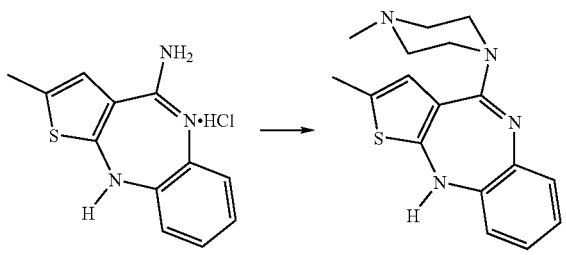

Intermediate 1

In a suitable three neck flask the following was added:

Dimethylsulfoxide (analytical): 6 volumes
Intermediate 1: 75 g
N-Methylpiperazine (reagent): 6 equivalents Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until about 5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

Preparation 2

Form II

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency≧97%, total related substances<0.5% and an isolated yield of >73%.

Preparation 3

Preparation of 2-methyl-4-(4-methyl-1-piperazinyl)-10H-thieno[2,3-b][1,5]benzodiazepine pamoate (olanzapine pamoate)

A. Olanzapine (3.12 g, 0.01 mole) was dissolved in tetrahydrofuran (50 ml) with heating. Pamoic acid (3.88 g, 0.01 mole) was dissolved in tetrahydrofuran (100 ml) with heating. The two solutions were mixed and filtered through a pad of celite while it is still warm. The yellow solution was transferred to a Buchi flask and evaporated under reduced pressure (bath temperature 50° C.). After about 50 ml of solvent had been removed ethanol (50 ml) was introduced and evaporation continued. A further 50 ml of ethanol was introduced after a further 50 ml of solvent had been collected. Evaporation was continued until crystallization commenced. The yellow crystals were collected by filtration and dried under high vacuum at 120° C. Mp 203–205° C. OK by 1H NMR, $^{13}$C NMR and MS. HPLC purity 99.61%

OK by 1H NMR, $^{13}$C NMR and MS. HPLC purity 99.61%
1H Spectrum Peaks, 8.4, s, 2p, s, 8.2, d, 2p, d, 7.9, s, 1p, s, 7.8, d, 2p, d, 7.2, t, 2p, t, 7.1, t, 2p, t, 6.9, m, 2p, 6.7, m, 1p, t?, 6.4, s, 1p, s, 4.8, s, 2p, s, 3.6, br, 4p, br, 3.3, br, 4p, br, 2.8, s, 3p, s, 2.3, s, 3p, s 13C Peaks, 171.4, 156.6, 154.6, 154.5, 143.7, 138.2, 135.1, 129.5, 128.9, 128.0, 126.9, 126.6, 125.8, 124.0, 123.1, 122.9, 121.8, 121.6, 119.3, 118.5, 117.8, 115.9, 51.9, 43.6, 42.0, 19.3, 14.4

Preparation 4

Preparation of 2-methyl-4-(4-methyl-1-piperazinyl)-10H-thieno[2,3-b][1,5]benzodiazepine pamoate dimethanolate (olanzapine pamoate dimethanolate)

Into a 250 ml beaker equipped with a magnetic stirrer was added dimethylsulfoxide (DMSO) (10 ml, 0.636 M), pamoic acid (2.49 g, 6.41 mmol), and olanzapine (2.0 g, 6.40 mmol). The slurry was stirred at 20–25° C. to dissolve. The solution was added over 10 minutes to a 250 ml three necked flask equipped with a mechanical stirrer containing methanol (100 ml) at 20–25° C. Shortly after starting the addition to methanol, the solution became turbid as crystals began to form. The solids increased as the addition continued. After the addition was completed, the temperature was adjusted to 5° C. over about 15 minutes and stirred for a 120 minutes. The slurry was filtered. The flask and wet cake were washed with methanol (25 ml). The product was dried in vacuo overnight at 50° C. to give 4.61 g of olanzapine pamoate dimethanolate as identified by X-ray powder diffraction (XRPD), TGA (8.2%), gas chromatography (GC) (8.6% methanol), and nuclear magnetic resonance (NMR) analysis (1:1 salt).

Preparation 5

Preparation of 2-methyl-4-(4-methyl-1-piperazinyl)-10H-thieno[2,3-b][1,5]benzodiazepine pamoate THF solvate (olanzapine pamoate THF solvate)

Into a 250 ml three neck flask equipped with a magnetic stirrer was added tetrahydrofuran (THF) (60 ml), pamoic acid (2.49 g, 6.41 mmol), and olanzapine (2.0 g, 6.40 mmol). The slurry was stirred at 20–25° C. to dissolve (about 20 min). To the THF solution was added methanol (30 ml) over 10 minutes. As soon as the addition for the mixture was completed, half of the slurry was filtered. The wet cake (1) was then dried in vacuo overnight at 50° C. to give 2.07 g. The remaining slurry was stirred for 2 hours at room temperature and filtered. The wet cake (2) was then dried in vacuo overnight at 50° C. to give 2.16 g. In both cases, the isolated material was identified as olanzapine pamoate THF solvate by XRPD, TGA (12.7–13.5%), and NMR analysis (12.2–12.9% THF, 1:1 salt).

Preparation 6

Preparation of 2-methyl-4-(4-methyl-1-piperazinyl)-10H-thieno[2,3-b][1,5]benzodiazepine pamoate monohydrate (olanzapine pamoate monohydrate)

Into a suitable beaker equipped with a magnetic stirrer was added dimethylsulfoxide (22 ml), pamoic acid (2.49 g, 6.41 mmol), and olanzapine (2.0 g, 6.40 mmol). The slurry was stirred at 20–25° C. to dissolve (about 20 minutes). The solution was added over 20 minutes to a 250 ml three-necked flask equipped with a mechanical stirrer and containing water (96 ml) at 40° C. After the addition was completed, the slurry was stirred about 20 minutes at 40° C., cooled to 20–25° C. over about 30 minutes, filtered and washed with water (25 ml). The product was dried in vacuo at 50° C. to give 4.55 g of olanzapine pamoate monohydrate by XRPD, TGA (3.0%), and titrimetric (KF=3.2%) analysis.

Preparation 7

A. Preparation of bis(2-methyl-4-(4-methyl-1-piperazinyl)-10H-thieno[2,3-b][1,5]benzodiazepine) pamoate acetone solvate (bis(olanzapine) pamoate acetone solvate)

Into a 100 ml three neck flask equipped with an agitator was added acetone (10 ml), pamoic acid (1.25 g, 3.22 mmol) and olanzapine (2.0 g, 6.4 mmol). The slurry was stirred at 20–25° C. about 60 min and filtered. The wet cake was washed with acetone (5 ml). The product was dried in vacuo at 40° C. to give bis(olanzapine) pamoate acetone solvate (3.24 g) by XRPD, TGA (7.0%), and NMR (3.7% acetone, 2:1 salt) analysis.

B. Preparation of bis(2-methyl-4-(4-methyl-1-piperazinyl)-10H-thieno[2,3-b][1,5]benzodiazepine) pamoate acetone solvate (bis(olanzapine) pamoate acetone solvate)

Into a 100 ml three-neck flask equipped with an agitator was added dimethylsulfoxide (10.8 ml) and pamoic acid (3.75 g, 9.65 mmol). The slurry was stirred at 20–25° C. to dissolve. The solution was added over 15–20 minutes to a 250 ml three-necked flask equipped with a mechanical stirrer and containing acetone (150 ml) and olanzapine (6.0 g, 19.2 mmol) at 50° C. After the addition was completed, the slurry was stirred about 20 minutes at 50° C. The slurry was cooled to 20–25° C. over about 60 minutes, stirred for 60 minutes and filtered. The wet cake was washed with acetone (15 ml). Half of the wet cake was reslurried in acetone (54 ml) for 2 hours at 20–25° C., filtered and washed with acetone (10 ml). The product was dried in vacuo at 35–40° C. to give bis(olanzapine) pamoate acetone solvate (4.54 g) by XRPD, TGA (5.8%), GC (5.57% acetone), and NMR analysis (2:1 salt).

Preparation 8

Preparation of bis(2-methyl-4-(4-methyl-1-piperazinyl)-10H-thieno[2,3-b][1,5]benzodiazepine)(bis(olanzapine) pamoate monohydrate)

Into a 100 ml three-neck flask equipped with an agitator was added dimethylsulfoxide (10.8 ml) and pamoic acid (3.75 g, 9.65 mmol). The slurry was stirred at 20–25° C. to dissolve. The solution was added over 15–20 minutes to a 250 ml three-necked flask equipped with a mechanical stirrer and containing acetone (150 ml) and olanzapine (6.0 g, 19.2 mmol) at 50° C. After the addition was completed, the slurry was stirred about 20 minutes at 50° C. The slurry was cooled to 20–25° C. over about 60 minutes, stirred for 60 minutes and filtered. The wet cake was washed with acetone (15 ml). Half of the wet cake was dried in vacuo at 35–40° C. to give bis(olanzapine) pamoate monohydrate (5.01 g) by XRPD, TGA (3.3%), GC, titrimetric (KF=2.2%) and NMR analysis (2:1 salt).

Preparation 9

Preparation of (2-methyl-4-(4-methyl-1-piperazinyl)-10H-thieno[2,3-b][1,5]benzodiazepine)dihydrate D A 100 g sample of technical grade olanzapine (see Preparation 1) was suspended in water (500 mL). The mixture was stirred at about 25° C. for about 5 days. The product was isolated using vacuum filtration. The product was identified as Dihydrate D olanzapine using x-ray powder analysis. Yield: 100 g. TGA mass loss was 10.2%.

Preparation 10

Preparation of (2-methyl-4-(4-methyl-1-piperazinyl)-10H-thieno[2,3-b][1,5]benzodiazepine)dihydrate E A 0.5 g sample of technical grade olanzapine was suspended in ethyl acetate (10 mL) and toluene (0.6 mL). The mixture was heated to 80° C. until all the solids dissolved. The solution was cooled to 60° C. and water (1 mL) was added slowly. As the solution cooled to room temperature, a crystal slurry formed. The product was isolated using vacuum filtration and dried under ambient conditions. The product was identified as Dihydrate E using x-ray powder analysis and solid state $^{13}$C NMR. TGA mass loss was 10.5%. Yield: 0.3 g.

Preparation 11

Preparation of (2-methyl-4-(4-methyl-1-piperazinyl)-10H-thieno[2,3-b][1,5]benzodiazepine)dihydrate B A 10 g sample of technical grade olanzapine was suspended in water (88 mL). The mixture was stirred at about 25° C. for 6 hours. The product was isolated using vacuum filtration. The product was identified as Dihydrate B olanzapine using x-ray powder analysis. Yield: 10.86 g.

The following abbreviations are used in the tabulated examples below:

| | |
|---|---|
| O = | olanzapine particle size undetermined |
| O—F = | olanzapine milled fine; particle size less than 5 μm |
| O—C = | olanzapine milled coarse; particle size from 20–60 μm |
| OPDM—C = | olanzapine pamoate dimethanolate milled coarse particle size from 20–60 μm |
| OPDM—F = | olanzapine pamoate dimethanolate milled fine; particle size less than 5 μm |
| OPMH = | olanzapine pamoate monohydrate |
| OPMH—F = | olanzapine pamoate monohydrate milled fine; particle size less than 5 μm |
| BOPM or BOP = | bis(olanzapine) pamoate monohydrate |
| BOPM—F or BOP=F = | bis(olanzapine) pamoate monohydrate milled fine particle size less than 5 μm |
| aq = | aqueous |
| PEG200 = | polyethylene glycol having an average mole cellular weight of 200 |
| EtOH = | ethanol |
| CHITOSAN ® = | deacetylated chitin, |
| low MW, high MW | low and high molecular weight |
| NaCMC = | sodium carboxymethyl cellulose, sodium salt |
| Wrt = | with respect to |
| BRIJ ®-52 = | polyoxoethylene(2)cetyl ether surfactant |
| Carnauba = | wax |
| G-1726 ® | polyosythylene (20)serbitol beeswax derivative |
| PLURONIC = | nonionic surfactants which are block copolymers of propylene oxide and ethylene oxide. The propylene oxide block is sandwiched between two ethylene oxide blocks. Poly(oxyethylene) groups on both ends of polyoxypropylene chain. $HO(CH_2CH_2O)_a(CHCH_3CH_2O)_bCH_2CH_2O)_cH$ |

The alphabetical designation explains the physical form of the product: 'L' for liquids, 'P' for pastes, 'F' for solid forms. The first digit (two digits in a three-digit number) in the numerical designation, multiplied by 300, indicates the approximate molecular weight of the hydrophobe). The last digit, when multiplied by 10, indicates the approximate ethylene oxide content in the molecule.

| | |
|---|---|
| NF = | National Formulary = meets standards for polaxamers which is the generic designation for pluronics |
| LF and D = | low foam version Includes: PLURONICS F68 PLURONICS F 68NF PLURONICS L121 PLURONICS L092 |
| MIGLYOL 810 = | triglycerides of the fractionated vegetable fatty acids C8 and C10 (caprylic/capric acids) |
| MIGLOYOL 812 = | differs from 810 only in the C8/C10 ratio. Has a higher C10 ratio and the viscosity and cloud point is higher. |
| MIGLOYOL 840 = | propylene glycol diester of saturated vegetable fatty acids with chain lengths C and C10 (capric/caprylic acids). |
| CREMAPHOR EL = | a derivative of castor oil and ethylene oxide polyethoxylated castor oil. A mixture of a hydrophobic portion containing ricinoleic acid esters, glycerol and polyglycol ethers, and castor oil and a hydrophilic portion containing polyethylene glycol and ethoxylated glycerol. |
| CHREMAPHORE RH40 = | 40 moles ethylene oxide per mole of hydrogenated castor oil. |
| CHREMAPHORE RH60 = | 60 moles ethylene oxide per mole of hydrogenated castor oil. |
| POVIDONE USP(K-30) = | polyvinyl pyrrolidone United States Pharmacopeia XXIII: k value: 30 (intrinsic viscosity) |
| a-tocopherol synonyms = | vitamin E, alpha tocopherol, 2,5,7,8-tetramethyl-2-(4',8',12'-trimethyltridecl)-6-chromanol |
| NMP = | 1-methyl-2-pyrrolidinone |
| CROTHIX = | PEG 150 pentoarythrityl tetrasterate |
| SYNCROWAX = | synthetic beeswax |
| POLAWAX = | emulsifying wax |
| Tween 20 = | polyoxyethylene 20 sorbitan monolaurate, a laurate ester of sorbitol. The 20 stands for 20 moles of ethylene oxide copolymerized with one mole of sorbitol. |
| Tween 80 = | polyoxyethylene 80 sorbitan monooleate, an oleate ester of sorbitol. The 80 stands for 80 moles of ethylene oxide copolymerized with one mole of sorbitole. |

EXAMPLE 1

PLURONICS®: PLURONIC® F68NF (50 g) was mixed in 111 ml of HLCP grade water. The mixture was intermittently stirred with a spatula and cooled in the freezer. A sonicator was used to help break up undissolved material. The mixture was cooled and stirred until a clear solution resulted. Olanzapine (300 mg) was mixed with 10 ml of the PLURONIC® solution with a spatula until homogenous. The mixture was kept refrigerated until used.

The following Examples were prepared using substantially the same procedure described in Example 1.

| Ex. No. | Active | Vehicle | Conc. of Active in vehicle |
|---|---|---|---|
| 2 | O—F | 45% PLURONIC F68NF, aq | 30 mg/ml |
| 3 | O—F | 45% PLURONIC F68, aq | 30 mg/g |
| 4 | O—F | 45% PLURONIC F68NF, aq | 90 mg/ml |
| 5 | O—F | 41% PLURONIC F68NF, aq | 30 mg/ml |
| 6 | O—F | 41% PLURONIC F68NF, aq | 90 mg/ml |
| 7 | O—C | 40% PLURONIC F68, aq | 40 mg/ml |
| 8 | O—F | 45% PLURONIC F68, aq | 31 mg/ml |
| 9 | O—F | 41% PLURONIC F68, aq. | 30 mg/ml |
| 10 | O—F | 41% PLURONIC F68, aq. | 90 mg/ml |
| 11 | O—F | 45% PLURONIC F68, aq. | 120 mg/ml |
| 12 | O—F | 41% PLURONIC F68, aq. | 120 mg/ml |

EXAMPLE 13

Sucrose diacetate hexaisobutyrate (SDHB): A solution of 10% ethanol and 90% SDHB was mixed together with a spatula in a beaker until homogenous. Milled olanzapine (150 mg) was weighed into a beaker. SDHB solution (5 ml) was added and stirred with a spatula until the olanzapine was uniformly mixed into the vehicle.

The following Examples were prepared using substantially the same procedure described in Example 13.

| Ex. No. | Active | Vehicle | Conc. of Active in vehicle |
|---|---|---|---|
| 14 | O—F | 90% SDHB, 10% EtOH | 30 mg/ml |
| 15 | O—F | 75% SDHB, 16.7% PEG 200, 8.3% EtOH | 30 mg/ml |
| 16 | O—F | 75% SDHB, 10% PEG 200, 15% EtOH | 30 mg/ml |
| 17 | O—F | 90% SDHB, 10% EtOH | 30 mg/ml |
| 18 | O—F | PEG200 (10% w/w), ethanol-200 proof (15% w/w), SDHB (75%) | 29 mg/g |

EXAMPLE 19

Chitosan®: Water (70 g) was weighed into a beaker. Lactic acid (1 g) was added then 2 g of Chitosan®, and lastly 300 mg olanzapine. The mixture was stirred with a spatula until uniform.

The following Examples were prepared using substantially the same procedure described in Example 19.

| Ex. No. | Active | Vehicle | Conc. of Active in vehicle |
|---|---|---|---|
| 20 | O—C | 96% H$_2$O, 1.4% Lactic acid, 2.7% low MW CHITOSAN | 30 mg/g |
| 21 | O—C | 96% H$_2$O, 1.4% Lactic acid, 2.7% high MW CHITOSAN | 30 mg/g |

EXAMPLE 22

CHITOSAN: Water (25 g) was weighed into a beaker. Lactic acid (0.5 g) was added, then 765 mg of olanzapine, and lastly 1 g of CHITOSAN. The mixture was stirred with a spatula until uniform.

The following Examples were prepared using the procedure described in Example 22.

| Ex. No. | Active | Vehicle | Conc. of Active in vehicle |
|---|---|---|---|
| 23 | O—C | 96% H$_2$O, 1.4% Lactic acid, 2.7% low MW Chitosan | 30 mg/g |
| 24 | O—C | 96% H$_2$O, 1.4% Lactic acid, 2.7% high MW Chitosan | 30 mg/g |

EXAMPLE 25

Miscellaneous: NaCMC (2 g) was measured into a beaker and 100 ml of water was added. The mixture was stirred at room temperature with a magnetic stir bar on a stir plate until all solids dissolved. Olanzapine (150 mg) was weighed into a beaker and 4.85 ml of NaCMC vehicle was added. The mixture was stirred with a spatula until homogenously mixed. The formulation was resuspended by shaking or stirring immediately before use.

The following Examples were prepared using the procedure described in Example 25.

| Ex. No. | Active | Vehicle | Conc. of Active in vehicle |
|---|---|---|---|
| 26 | O—F | 2% NaCMC, aqueous | 30 mg/ml |
| 27 | O | Na Aginate, H$_2$O | 10% |

EXAMPLE 28

Oil: Milled olanzapine (120 mg) was weighed into a beaker and 3.88 ml of MIGLYOL® 812 oil was added. The mixture was stirred with a spatula until homogenous. The solids in formulation settled easily such that formulation was resuspended by shaking or stirring immediately before use.

The following Examples were prepared using the procedure described in Example 28.

| Ex. No. | Active | Vehicle | Conc. of Active in vehicle |
|---|---|---|---|
| 29 | O—F | MIGLYOL 812 | 30 mg/ml |
| 30 | OPDM-C | Sesame oil | 30 mg/ml |
| 31 | OPDM-F | MIGLYOL 812 | 30 mg/ml |
| 32 | OPDM-C | MIGLYOL 812 | 30 mg/ml |
| 33 | O—F | Sesame oil | 30 mg/ml |
| 34 | O—F | Sesame oil | 30 mg/ml |
| 35 | O-dihydrated | Sesame oil | 30 mg/ml |
| 36 | O—C | Sesame oil | 30 mg/ml |
| 37 | O | Sesame oil, 0.5 g Al-monostearate-nongelled | 30 mg/ml |
| 38 | O | Sesame oil; Al-monostearate (30 mg/ml)-non-gelled | 30 mg/ml |
| 39 | O—C | 95% MIGLYOL® 840, 5% Oleic acid | 30 mg/ml |
| 40 | O—C | 90% Sesame oil, 10% Oleic acid | 30 mg/ml |

EXAMPLE 41

Oleic Acid: Oleic acid (0.54 ml) and 300 mg olanzapine were warmed together. MIGLYOL® 840 oil (9.2 ml) was then added and all solids were dissolved by gently warming.

The following Examples were prepared using substantially the same procedure described in Example 41.

| Ex. No. | Active | Vehicle | Conc. of Active in vehicle |
|---|---|---|---|
| 42 | O—C | Oleic acid (2M wrt O), MIGLYOL 840 | 30 mg/ml |
| 43 | O—C | Oleic acid (2M wrt O) in MIGLYOL 840 | 40 mg/ml |
| 44 | O—C | Oleic acid (2M wrt O) in MIGLYOL 840 | 30 mg/ml |
| 45 | O—C | Oleic acid (2M wrt O) in MIGLYOL 840 | 31 mg/ml |
| 46 | O—F | Oleic acid (100 ml/ml); Sesame oil | 30 mg/ml |
| 47 | O—C | CREMAPHOR EL | 40 mg/ml |
| 48 | O—C | CREMAPHOR EL | 31 mg/ml |
| 49 | O—C | CREMAPHOR EL | 30 mg/ml |
| 50 | O—F | CREMAPHOR EL | 30 mg/ml |
| 51 | O—C | Ethyl oleate | 30 mg/ml |
| 52 | O—C | Benzyl alcohol | 30 mg/ml |
| 53 | O—C | Benzyl benzoate | 30 mg/ml |
| 54 | O | PLURONIC L121 | 30 mg/g |
| 55 | O—F | PLURONIC L092 | 30 mg/ml |
| 56 | O—F | PLURONIC L121 | 30 mg/ml |

EXAMPLE 57

Gelled Oil: To gel the oil, 25 g of aluminum monostearate was added to 475 g of sesame oil in a flask. The oil was mixed with a static mixer with a stainless steel propeller, while warming in an oil bath to 155° C. for 20 minutes. Nitrogen gas was allowed to flow over the system during the process. The oil was then allowed to cool to room temp. Milled olanzapine (120 mg) was weighed into a beaker and 3.88 ml of gelled sesame oil was added The mixture was stirred well with a spatula until homogenous.

The following Examples were prepared using substantially the same procedure described in Example 57.

| Ex. No. | Active | Vehicle | Conc. of Active in vehicle |
|---|---|---|---|
| 58 | O—F | 95% gelled Sesame oil, 5% aluminum monostearate | 30 mg/ml |
| 59 | O—C | 95% gelled Sesame oil, 5% aluminum monostearate | 30 mg/ml |
| 60 | O-dihydrated | 95% gelled Sesame oil, 5% aluminum monostearate | 30 mg/ml |

EXAMPLE 61

Wax/Oil: White wax (400 mg) was measured into a beaker and 3.6 g of MIGLYOL® 812 oil was added. The mixture was warmed in a water bath at around 80° C. until the wax was melted. Then stirred with a spatula until homogenous. Milled olanzapine (1 g) was added of to the beaker and stirred with a spatula until mixed homogenously. The mixture was allowed to cool to room temperature while mixing.

The following Examples were prepared using substantially the same procedure described in Example 61. In some cases the mixture was homogenized with a hand held homogenizer to reduce larger particle sizes and aggregates of the active ingredient.

| Ex. No. | Active | Vehicle | Conc. of Active in vehicle |
|---|---|---|---|
| 62 | O—F | 90% MIGLYOL 812, 10% White wax | 200 mg/ml |
| 63 | O—F | 90% MIGLYOL 812, 10% G-1726 | 300 mg/ml |
| 64 | O—F | 90% MIGLYOL 812, 10% G-1726 | 400 mg/ml |
| 65 | O—F | 90% MIGLYOL 812, 10% White wax | 300 mg/ml |
| 66 | O—F | 90% MIGLYOL 812, 10% G-1726 | 200 mg/ml |
| 67 | O—F | 57.5% MIGLYOL 812, 2.5% Ethyl Oleate, 10% White wax | 300 mg/ml |
| 68 | O—F | 90% MIGLYOL 812, 10% White wax | 400 mg/ml |
| 69 | O—F | 50% MIGLYOL 812, 50% BRIJ 52 | 300 mg/ml |
| 70 | O—F | 80% MIGLYOL 812, 20% Polawax | 300 mg/ml |
| 71 | OPDM-F | 90% MIGLYOL 812, 10% G-1726 | 200 mg/ml |
| 72 | O—F | 95% MIGLYOL 812, 5% G-1726 | 300 mg/ml |
| 73 | O—F | 95% MIGLYOL 812, 5% White wax | 300 mg/ml |
| 74 | OPDM-F | 90% MIGLYOL 812, 10% G-1726 | 150 mg/ml |
| 75 | O—F | 90% MIGLYOL 812, 10% syncrowax | 300 mg/ml |
| 76 | O—F | 65% MIGLYOL 812, 35% Crothix | 300 mg/ml |
| 77 | OPMH-F | 90% MIGLYOL 812, 10% White wax | 300 mg/ml |
| 78 | OPMH-F | 90% MIGLYOL 812, 10% Polawax | 300 mg/ml |
| 79 | OPMH-F | 80% MIGLYOL 812, 20% White wax | 300 mg/ml |
| 80 | OPMH-F | 90% MIGLYOL 812, 10% White wax | 400 mg/ml |
| 81 | OPMH-F | 90% MIGLYOL 812, 10% Polawax | 400 mg/ml |
| 82 | OPMH-F | 95% MIGLYOL 812, 5% White wax | 400 mg/ml |
| 83 | OPMH-F | 90% MIGLYOL 812, 10% Polawax | 350 mg/ml |
| 84 | OPMH-F | 95% MIGLYOL 812, 5% White wax | 350 mg/ml |
| 85 | OPMH-F | 95% MIGLYOL 812, 5% White wax | 350 mg/ml |
| 86 | OPMH-F | 85% MIGLYOL 812, 15% Polawax | 300 mg/ml |
| 87 | OPMH-F | 90% MIGLYOL 812, 10% G-1726 | 300 mg/ml |
| 88 | OPMH-F | 90% MIGLYOL 812, 10% White wax | 300 mg/ml |
| 89 | BOPM-F | 90% MIGLYOL 812, 10% White wax | 300 mg/ml |
| 90 | BOPM-F acetone solvate | 90% MIGLYOL 812, 10% White wax | 300 mg/ml |
| 91 | BOPM-F DMSO impurities | 90% MIGLYOL 812, 10% White wax | 300 mg/ml |
| 92 | O | 90% MIGLYOL 812, 10% G-1726 | 300 mg/g |
| 93 | O | 90% MIGLYOL 812, 10% G-1726, 0.03% Propyl Gallate | 300 mg/g |
| 94 | OPDM-F | 90% MIGLYOL 812, 10% G-1726 | 200 mg/g |
| 95 | BOPM-F | 90% MIGLYOL 812, 10% white wax | 30% |
| 96 | OPMH-F | 90% MIGLYOL 812, 10% white wax | 30% |

EXAMPLE 97

Lecithin: Olanzapine (500 mg) plus 12.0 g lecithin was stirred well with spatula for approximately 15 minutes to ensure homogeneity.

EXAMPLE 98

Lecithin+∝-tocopherol: Lecithin (8.9972 g) plus 1.0204 g ∝-tocopherol was stirred well and kept overnight in the refrigerator. The mixture was stirred well, then 300.7 mg of olanzapine was added and mixed well.

EXAMPLE 99

Lecithin/NMP: Olanzapine (500 mg) was dissolved in 3 ml of N-methyl pyrrolidone (NMP). Lecithin (9 ml) was added and stirred well with a spatula for approximately 15 minutes to obtain a homogenous mix.

EXAMPLE 100

Cholesterol/POVIDONE USP (K-30)/ethyl cellulose/NMP: Olanzapine (500 mg), ethyl cellulose (0.062 g) and NMP (5 ml) were stirred well and gently warmed for 2–3 minutes until a clear solution was obtained. POVIDONE USP (K-30) (0.309 g) and cholesterol (2.475 g) were then added to obtain a thick gum-like formulation, dry in consistency.

EXAMPLE 101

Cholesterol/POVIDONE USP (K-30)/ethyl cellulose/NMP: Cholesterol (2.475 g), 0.3098 g of POVIDONE USP (K-30), 0.0622 g of ethyl cellulose and 9.1686 g NMP were weighed into a 25 ml beaker. The materials contained in the beaker were mixed thoroughly and warmed slightly to dissolve any insoluble materials. Caution was taken to use the minimal exposure to heat for solubilizing purposes. The clear solution was cooled and to it was added 500 mg of olanzapine which was thoroughly mixed, giving a clear pale yellow solution.

EXAMPLE 102

Lecithin/Cholesterol/POVIDONE USP (K-30)/ethyl cellulose/NMP: 0.2511 g of POVIDONE USP (K-30) was weighed into a beaker. To it was added 300.5 mg of olanzapine-coarse, 28.5 mg of ethyl cellulose and 2.008 g of cholesterol. This dry mixture was stirred well. To this dry mixture was added 0.7463 g of ∝-tocopherol and this mixture was stirred well. To this was added 3.3806 g lecithin, mixed well. Then another 3.0825 g of lecithin was added and mixed well again.

EXAMPLE 103

Lecithin/Cholesterol/POVIDONE USP (K-30)/ethyl cellulose/NMP: Olanzapine-coarse (300.7 mg.), 2.5821 g. of NMP and 25.4 mg. of ethyl cellulose were stirred well. To these were added 248.0 mg of POVIDONE USP (K-30), 2.0008 g of cholesterol and 2.6020 g of lecithin. This formulation was stirred well. The mixture separated into layers and was warmed in a 37° C. bath for 5 minutes. A soft lump-like formation coagulated in the thick solution. Lecithin (2.5074 g) was added and mixed well. Eventually the formulation seemed to lose the gel-like coagulation and formed a suspension of olanzapine.

The following examples were prepared using substantially the same procedures described in Examples 97–103, above.

| Ex. No. | Active | Vehicle | Conc. of Active in vehicle | Example |
|---|---|---|---|---|
| 104 | O—C | Lecithin | 41.6 mg/g | 95 |
| 105 | O—C | 10% alph-tocopherol, 90% Lecithin | 30 mg/ml | 96 |
| 106 | O | 25% NMP, 75% Lecithin | 41.6 mg/ml | 97 |
| 107 | O | 75% Lecithin, 25% NMP | 30 mg/ml | 97 |
| 108 | O—C | 25% NMP, 75% Lecithin | 41 mg/g | 97 |
| 109 | O—C | 27.8% NMP, 72.2% Lecithin | 30 mg/ml | 97 |
| 110 | O | 31.5% Cholesterol, 3.9% POVIDONE USP (K-30), 0.8% Ethyl cellulose, 63.7% NMP | 63.7 mg/g | 98 |
| 111 | O | 20.6% Cholesterol, 2.6% POVIDONE USP (K-30), 0.5% Ethyl cellulose, 42.7% NMP, 34.6% Lecithin | 15.0 mg/g | (a) 98 (b) followed by dilution with lecithin |
| 112 | O—C | 2.6% POVIDONE USP (K-30), 20.6% Cholesterol, 0.5% ethyl cellulose, 76.3% NMP | 41.6 mg/g | 99 |
| 113 | O—C | 19.7% Cholesterol, 2.46% POVIDONE USP (K-30), 0.54% Ethyl cellulose, 39.8% NMP, 33.5% Lecithin | 39.8 mg/g | 99 |
| 114 | O—C | 7.9% alpha-tocopherol, 0.3% Ethyl cellulose, 2.63% POVIDONE USP (K-30), 21% Cholesterol, 68.1% Lecithin, | 31.55 mg/g | (a) 100 (b) followed by dilution with lecithin |
| 115 | O—C | 0.25% Ethyl cellulose, 2.5% PVP, 20% Cholesterol, 7.7% alpha-tocopherol, 69.5% Lecithin | 29 mg/g | 103 |
| 116 | O | 66.8% Lecithin, 0.25% ethyl cellulose, 2.5% POVIDONE, USP (K-30), 20% Cholesterol, 20% alpha-tocopherol | 30 mg/ml | 100 |
| 117 | O—C | 25.9% NMP, 0.26% Ethyl cellulose, 2.49% POVIDONE USP (K-30), 20.1% Cholesterol, 51.3% Lecithin, | 30 mg/ml | 101 |

EXAMPLE 118

Olanzapine-Cholesterol Microparticle 5 g (1%) polyvinyl alcohol (PVA) was added to 500 ml of deionized water. The solution was stirred with a magnetic stir bar and warmed for several hours until all of the PVA dissolved. The mixture was allowed to cool to room temperature. The solution was poured into a square plastic container and stirred with an overhead stirrer at 450 RPM. 1.2 g of olanzapine and 8.8 g of cholesterol was dissolved in 100 ml of methylene chloride. The PVA solution was added and the mixture was stirred for 18 hours.

Microparticle Collection

Method 1: A PVA/olanzapine solution was poured through 100 and 230 mesh sieves (USA std.) respectively. The large and fine sections were discarded. Particles were washed from the 230 sieve with water into a Buchner funnel with a Whatman #4 filter paper and vacuum filtered. The particles were transferred to a weighing dish and allowed to air dry. The particle size collected: >63 μm–<150 μm.

Method 2: A PVA/olanzapine solution was vacuum filtered with a Buchner funnel through Whatman #4 filter paper and washed with water. The particles were transferred to a weighing dish and allowed to air dry. The particles were dry sieved through a 30 mesh sieve (USA std.) to remove any large particles.

Method 3: A PVA/olanzapine solution was poured through 230 mesh sieve (USA std.). The particles were washed from the sieve with water into a Buchner funnel with a Whatman #4 filter paper and vacuum filtered. Particles were transferred to a weighing dish and allowed to air dry. The particle size collected: >63 μm.

Method 4: A PVA/olanzapine solution was poured through 230 mesh sieve (USA std.). The particles were washed from the sieve with water into a Buchner funnel with a Whatman #4 filter paper and vacuum filtered. Particles were transferred to a weighing dish and allowed to air dry. The dry particles were sieved through 100 mesh sieve (USA std.). The particle size collected: >63 μm–<150 μm.

Method 5: A PVA/olanzapine solution was poured through 100 mesh sieve (USA std.). The particles were washed from the sieve with water into a Buchner funnel with a Whatman #4 filter paper and vacuum filtered. Particles were transferred to a weighing dish and allowed to air dry. The particle size collected: >150 μm. The sieved PVA/olanzapine solution was centrifuged and decanted. The pellet was vacuum filtered with a Buchner funnel through Whatman #4 filter paper, transferred to a weighing dish and air dried. Particle size collected <150 μm.

Method 6: A PVA/olanzapine solution was vacuum filtered with a Buchner funnel through Whatman #4 filter paper and washed with water. The particles were transferred to a weighing dish and allowed to air dry.

The product was assayed for potency by high performance liquid chromatography.

| Ex. No. | Active | Excip. | Other excip./concs. | Conc. of Active (theoretical) | Solvent for active | Extraction bath | Stir speed | Stir time | Micro-particle collection |
|---|---|---|---|---|---|---|---|---|---|
| 119 | O—F | Choles. | — | 9.9% | 100 ml. $CH_2Cl_2$ | 500 ml. 1% PVA | 450 rpm | 18 hrs | Gravity filter; air dry; sieve through 30 mesh sieve |
| 120 | O—F | Choles. | — | 10.2% | 100 ml. $CH_2Cl_2$ | 500 ml. 1% PVA cooled to 20 C. | 500 rpm | 4 hrs | Method 2 |
| 121 | O-unmill | Choles. | — | 8.1% | 10 ml. $CH_2Cl_2$ | 100 ml. 1% PVA cooled to 20 C. | 500 rpm | 3 hrs | Method 6 |
| 122 | O—F | Choles. | | 28.9% | 15 ml. $CH_2Cl_2$ | 50 ml. 1% PVA | 260 rpm | 3.5 hrs | Method 1 |
| 123 | O—F | Choles. | | <100 > 230 = 15% | 50 ml. $CH_2Cl_2$ | 250 ml. 1% PVA | 450 rpm | 16 hrs | Method 1 |
| 124 | O—F | Choles. | | <100 > 230 = 26.4% | 200 ml. $CH_2Cl_2$ | 750 ml. 1% PVA | 250 rpm | 16 hrs | Method 1 |
| 125 | O—F | Choles. | | <100 > 230 = 21.4% | 200 ml. $CH_2Cl_2$ | 750 ml. 1% PVA | 250 rpm | 16 hrs | Method 1 |
| 126 | O—C | Choles. | ethyl oleate (10%) | 17.2% | 60 ml. $CH_2Cl_2$ | 0.5% PVA | 428 rpm | 7 hrs | Method 1 |
| 127 | O—C | Choles. | ethyl oleate (15%) | 15.4% | 60 ml. $CH_2Cl_2$ | 0.5% PVA | 393 rpm | 7 hrs | Method 1 |
| 128 | O—C | Choles. | ethyl oleate (5%) | 16.9% | 60 ml. $CH_2Cl_2$ | 0.5% PVA | 397 rpm | 7 hrs | Method 1 |
| 129 | O—F | Choles. | ethyl oleate (10%) | (25%) | 260 ml. $CH_2Cl_2$ | 1200 ml. 1% PVA | 430–481 rpm | 18 hrs | Method 1 |
| 130 | O—F | Choles. | | (50%) | 25 ml. $CH_2Cl_2$ | 1% PVA | 453 rpm | 14.5 hrs | Method 1 |
| 131 | O—F | Choles. | ethyl oleate (2.5%) | (50%) | 25 ml. $CH_2Cl_2$ | 1% PVA | 457 rpm | 14.5 hrs | Method 3 |
| 132 | O—F | Choles. | — | 23.9% | 30 ml $CH_2Cl_2$ | 250 ml 1% PVA | 400 rpm | 16 hrs | Method 4 |
| 133 | O—F | Choles. | — | 29.6% | 35 ml $CH_2Cl_2$ | 250 ml 1% PVA | 400 rpm | 16 hrs | Method 4 |
| 134 | O—F | Choles. | 10% oleic acid | 34.5% | 25 ml $CH_2Cl_2$ | 250 ml 1% PVA | 400 rpm | 16 hrs | Method 4 |
| 135 | O—F | Choles. | 10% oleic acid | 32.3% | 30 ml $CH_2Cl_2$ | 250 ml 1% PVA | 400 rpm | 16 hrs | Method 4 |
| 136 | O—F | Choles. | — | 20.5% | 200 ml $CH_2Cl_2$ | 750 ml 1% PVA | 380 rpm | 16 hrs | Method 4 |
| 137 | O—F | Choles. | — | 37.3% | 200 ml $CH_2Cl_2$ | 750 ml 1% PVA | 250 rpm | 16 hrs | Method 4 |
| 138 | O—F | Choles. | — | 23.5% | 200 ml $CH_2Cl_2$ | 750 ml 1% PVA | 300 rpm | 16 hrs | Method 4 |

-continued

| Ex. No. | Active | Excip. | Other excip./concs. | Conc. of Active (theoretical) | Solvent for active | Extraction bath | Stir speed | Stir time | Micro-particle collection |
|---|---|---|---|---|---|---|---|---|---|
| 139 | O—F | Choles. | — | 31.8% | 200 ml CH$_2$Cl$_2$ | 750 ml 1% PVA | 400 rpm | 16 hrs | Method 4 |
| 140 | O—F | Choles. | 2.5% ethyl oleate | 25.3% | 50 ml CH$_2$Cl$_2$ | 200 ml 1% PVA | 400 rpm | 16 hrs | Method 4 |
| 141 | O—F | Choles. | 10% ethyl oleate | 24.6% | 50 ml CH$_2$Cl$_2$ | 200 ml 1% PVA | 400 rpm | 16 hrs | Method 4 |
| 142 | O—F | Choles. | 20% ethyl oleate | 24.7% | 50 ml CH$_2$Cl$_2$ | 200 ml 1% PVA | 400 rpm | 16 hrs | Method 4 |
| 143 | O—F | Choles. | 2.5% ethyl oleate | 19.3% | 50 ml CH$_2$Cl$_2$ | 200 ml 1% PVA | 380 rpm | 16 hrs | Method 4 |
| 144 | O—F | Choles. | 10% G-1726 ® | 28.9% | 50 ml CH$_2$Cl$_2$ | 200 ml 1% PVA | 375 rpm | 16 hrs | Method 4 |
| 145 | O—F | Choles. acetate | — | (30%) | 30 ml CH$_2$Cl$_2$ | 320 ml 1% PVA | 346 rpm | | Method 6 |
| 146 | O—F | Choles. acetate | — | 5.2% | 10 ml CH$_2$Cl$_2$ | 60 ml 1% PVA | 260 rpm | 3 hrs | Method 2 |
| 147 | O—F | Choles. acetate | | 4.3% | 5 ml. CH$_2$Cl$_2$ | 200 ml 1% PVA 20 C. sq. container | 400 rpm | 6 hrs | Method 2 |
| 148 | O—F | Choles. Hemi succinate | | (30%) | 30 ml. CH$_2$Cl$_2$ | 300 ml 1% PVA | 353 rpm | | Method 6 |
| 149 | O—F | Choles. Hemi succinate | | 8.8% | 5 ml. CH$_2$Cl$_2$ | 100 ml 1% PVA | 400 rpm | 3 hrs | Method 2 |
| 150 | O—F | Choles. Hemi succinate | | 9.3% | 25 ml. CH$_2$Cl$_2$ | 500 ml 1% PVA 20 C. sq. container | 400 rpm | overnight | Method 2 |
| 151 | O—F | Choles. Hemi succinate | | 10% | 35 ml CH$_2$Cl$_2$ | 250 ml 1% PVA sq plastic container | 450 rpm | 4 hrs | Allowed to sit overnight in PVA, Method 1 |
| 152 | O—F | Choles. Hemi | | 9.9% | 50 ml CH$_2$Cl$_2$ | 250 ml 1% PVA sq plastic container | 600 rpm | 15 hrs | Method 1 |
| 153 | O—F | Choles. Hemi succinate | | >150 = 8.4% <150 = 8.9% | 50 ml CH$_2$Cl$_2$ | 250 ml 1% PVA sq plastic container | 650 rpm | 15 hrs | Method 5 |
| 154 | O—F | Choles. Hemi succinate | | >150 = 9.0%, <150 > 63 = 8.2%, <63 = 7.8% | 50 ml. CH$_2$Cl$_2$ | 250 ml 1% PVA sq plastic container | 650 rpm | 15 hrs | Method 1, Method 5 |
| 155 | O—F | Choles. Hemi succinate | | 9.9% | 50 ml CH$_2$Cl$_2$ | 250 ml 1% PVA sq plastic container | 650 rpm | 15 hrs | Method 1 |
| 156 | O—F | Choles. Oleate | | 2.3% | 4 ml CH$_2$Cl$_2$ | 200 ml 1% PVA | 400 rpm | 3.5 hrs | Method 2 |
| 157 | O—F | Choles. Oleate | — | 8.0% | 10 ml CH$_2$Cl$_2$ | 60 ml 1% PVA | 260 rpm | 3 hrs | Method 1 |
| 158 | O—F | Choles. Palmitate | | (30%) | 40 ml. CH$_2$Cl$_2$ | 300 ml 1% PVA | 350 rpm | | Method 6 |
| 159 | O—F | Choles. palmitate | | 12.0% | 50 ml CH$_2$Cl$_2$ | 250 ml 1% PVA | | overnight | Method 2 |
| 160 | O—F | Choles. palmitate | | 7.3% | 10 ml CH$_2$Cl$_2$ | 200 ml 1% PVA | 400 rpm | 3.5 hrs | Method 2 |
| 161 | O—F | Choles. palmitate | | 10.8% | 50 ml CH$_2$Cl$_2$ | 250 ml 1% PVA | 350 rpm | 15 hrs | Method 1 |
| 162 | O—F | Choles. palmitate | | 11.9% | 50 ml CH$_2$Cl$_2$ | 250 ml 1% PVA | 350 rpm | 15 hrs | Method 5 |
| 163 | O—F | Choles. Stearate | | 7.4% | 5 ml CH$_2$Cl$_2$ | | | 3.5 hrs | |
| 164 | O—F | Choles. Stearate | | (13%) | 40 ml CH$_2$Cl$_2$ | 250 ml 1% PVA | 400 rpm | overnight | Method 2 |

*"<100, >230 = (XXX%)" stands for a sieved lot with a particle size range less than 100 mesh and greater than 230 mesh. This sieve cut was assayed for potency which is the percent reported
**">150 = (XXX%) < 150 = (XXX%)" stands for the sieve cut greater than 150 uμ = assayed concentration of olanzapine and the sieve cut less than 150 uμ = assayed concentration of olanzapine

EXAMPLE 165

Spray-Drying

Olanzapine (0.5 g milled) and 4.5 g of cholesterol were dissolved in 50 ml of methylene chloride. This solution was spray dried with a lab scale Yamato spray dryer with a 60 cm long drying column. The dryer conditions were set as follows: inlet temp.=50° C., outlet temperature=33° C., air flow volume=55 m$^3$, spray atomizing volume=0.55 Kgf/cm$^3$. The microparticles were collected in a vial at the outlet and sieved to 63–150 μm particle size and assayed for potency by high performance liquid chromatography.

The following examples were prepared using substantially the same procedure as described in Example 164.

| Ex. No. | Active | Excip. | Other excip./ concs. | Conc. of Active (theoretical) | Solvent for active | Inlet Temp (° C.) | Outlet Temp (° C.) | Air Flow Volume (m$^3$/min) | Spray atomization volume (Kgf/cm$^3$) |
|---|---|---|---|---|---|---|---|---|---|
| 166 | O | Choles. | | 8.6% | 50 ml CH$_2$Cl$_2$ | 50 | 33 | 0.55 | 0.5 to 0.6 |
| 167 | O—F | Choles. | | 29.5% | 100 ml CH$_2$Cl$_2$ | 50 | 29 | 0.53 | 0.2 |
| 168 | O—F | Choles. | 2.5% Ethyl Oleate | 29.5% | 100 ml CH$_2$Cl$_2$ | 60 | 40 | 0.55 | 0.2 |
| 169 | O | Choles. Acetate | 33.3% Tristearin | (33.3%) | CHCl$_3$ | 40 | 25 | 0.65 | 0.1 to 0.4 |
| 170 | O | Choles. Acetate | | (50%) | CHCl$_3$ | 40 | 25 | 0.65 | 0.1 to 0.4 |

Summary of Methods

Formulations were mixed and loaded into 5 ml syringes. A tip was cut from a disposable plastic pipet and fitted onto the syringe. Dialysis tubing was cut into 5–6 cm length and kept moist in a beaker of water. One end of the tubing was clipped off with a tubing clip. The tubing was tared on a scale and from the syringe one ml of formulation was dispensed into the tubing. The open end was clipped and the final weight was recorded. The filled dialysis tubing was placed in a 900 ml dissolution vessel filled with 250 ml Dulbecco's phosphate buffered saline pH 7.4 at 37° C. The vessels were placed in a Vankel dissolution apparatus with paddles rotating at 50 RPM. Samples were pulled manually by stopping the rotation of the paddles and removing 2 ml aliquot samples with pipets. Samples were pulled at 2, 4, 8, 12, 24, 48, and consecutive 24 hour intervals from 48 hours up to 4 weeks in duration. At 2, 4, 8, and 12 hour samples the media was replaced with 2 ml of fresh buffer. At each 24 hour time point the entire media volume was replaced with fresh media pre-warmed to 37° C. The samples were placed directly into HPLC vials and assayed for potency by high pressure liquid chromatography.

Formulations were tested using the release assay described above and were found to have an acceptable prolonged sustained release rate of active at from 48 hours to up to 4 weeks.

Rabbit Assay

New Zealand White rabbits were selected for the evaluation of depot formulations because the size of their leg muscles facilitates dose administration and evaluation of the injection site.

Three rabbits of the same sex were used for each formulation with selection based on availability. The rabbits were at least 5 months old and weigh between 2.5 to 5 kg. Rabbits were given a single injection with a 20- or 21-gauge needle into the biceps femoris. The dose volume varied with the concentration of the formulation but did not exceed 2 mL per injection. The rabbits were given 10 mg of olanzapine/kg body weight.

A 2 mL blood sample was collected from the medial ear artery or jugular vein into heparinized collection tubes once prior to dose administration and at 4 hours after dose administration and again daily after 1, 2, 7, 10, and 14 days. Plasma was harvested and plasma concentration of olanzapine was determined by HPLC.

Formulations of the instant invention were tested in the rabbit assay and found to show effective concentrations of olanzapine of up to 14 days.

Dog Assay

The beagle dog was selected because much is known about the pharmacokinetics of olanzapine in dogs. Since there is no difference in the pharmacokinetic of olanzapine between the sexes, dog selection was not based on sex. Three dogs (male or female) were used for each formulation. The dogs were adults (>6 months old) and weighed between 8 to 21 kg. The dogs were given a single injection with a 20 or 21 gauge needle into the gluteal or biceps femoris muscle. The dose volume varied with the concentration of the formulation but did not exceed 2 mL per injection. The dogs were given 10 mg of olanzapine/kg of body weight.

At each time point, a 2 mL blood sample was collected from the jugular vein into heparanized collection tubes. Blood samples were collected once prior to dose administration and at various time points after dose administration throughout the 28-day period. Typical time points are at 0.5, 1, 2, 4, 8, and 24 hours after dose administration and once daily after 2, 4, 7, 14, 21, and 28 days. Plasma was harvested and plasma concentration of olanzapine was determined by HPLC.

Formulations of the instant invention were tested in the dog assay and found to show effective concentrations of olanzapine at up to 28 days.

We claim:

1. A formulation comprising olanzapine pamoate monohydrate as an active ingredient and one or more carriers selected from the group consisting of an oleaginous carrier and cholesterol microsphere carrier wherein said formulation has a prolonged sustained release of greater than 7 days and up to 30 days, and a burst release of less than 15% of the active ingredient.

2. A formulation as claimed in claim 1 wherein said carrier is oleaginous.

3. A formulation as claimed by claim 1 wherein the formulation further comprises one or more pharmaceutically acceptable excipients.

4. A formulation as claimed by claim 3 wherein the pharmaceutically acceptable excipient is selected from the group consisting of a gelling agent and an antihydration agent.

5. A formulation as claimed in claim 1 wherein the carrier is a cholesterol microparticle.

6. A formulation as claimed in claim 5 wherein the microparticle is a microsphere.

7. A formulation as claimed in claim 5 wherein the cholesterol is selected from the group consisting of cholesterol, cholesterol palmitate, cholesterol oleate, cholesterol stearate, and cholesterol hemisuccinate.

8. A formulation as claimed in claim 5 wherein the microspheres have a particle size of from 20 to 500 μm.

9. A formulation as claimed in claim 8 wherein the particle size is from 30 to 200 μm.

10. A formulation as claimed in claim 6 wherein the particle size is from 40 to 100 μm.

11. A formulation as claimed in claim 5 wherein the microspheres are administered in an oleaginous carrier.

12. A formulation as claimed in claim 1 wherein the active ingredient is milled.

13. A formulation comprising olanzapine pamoate monohydrate as an active ingredient, and one or more carriers.

14. A formulation as claimed in claim 13 wherein the olanzapine pamoate monohydrate has a particle size of from about 20 to about 60 μm.

15. A formulation as claimed in claim 13 wherein the olanzapine pamoate monohydrate has a particle size of from about 5 to about 20 μm.

16. A formulation as claimed in 13 wherein said formulation has a prolonged sustained release of greater than 7 days and up to 30 days, and a burst release of less than 15% of the active ingredient.

* * * * *